United States Patent [19]
Barbet et al.

[11] Patent Number: 5,256,395
[45] Date of Patent: Oct. 26, 1993

[54] AFFINITY ENHANCEMENT IMMUNOLOGICAL REAGENTS FOR IN VIVO DETECTION AND KILLING OF SPECIFIC TARGET CELLS

[75] Inventors: Jacques Barbet; Michel Delaage; Jean-Marc Le Doussal, all of Marseilles, France

[73] Assignee: Immunotech Partners, Marseilles, France

[21] Appl. No.: 96,829

[22] Filed: Sep. 10, 1987

[30] Foreign Application Priority Data

Sep. 19, 1986 [FR] France .................. 86 13146

[51] Int. Cl.⁵ .................. A61K 39/395; A61K 49/02
[52] U.S. Cl. .................. 424/9; 424/1.1; 424/85.8; 424/85.91
[58] Field of Search .................. 424/9, 1.1, 85, 86, 424/4, 88, 90, 91, 94.1, 85.8, 85.91; 436/548, 804, 819, 813, 547, 543, 822; 530/335, 387, 388, 389, 390, 300, 391, 807, 387.3, 388.2, 388.25, 388.8, 388.9, 391.9

[56] References Cited

U.S. PATENT DOCUMENTS

| | | |
|---|---|---|
| 3,927,193 | 12/1975 | Hansen et al. |
| 4,331,647 | 5/1982 | Goldenberg |
| 4,401,764 | 8/1983 | Smith |
| 4,433,059 | 2/1984 | Chang et al. |
| 4,444,878 | 4/1984 | Paulus |
| 4,446,233 | 5/1984 | Auditore-Hargreaves et al. |
| 4,454,106 | 6/1984 | Gansow et al. |
| 4,470,925 | 9/1984 | Auditore-Hargreaves |
| 4,472,509 | 9/1984 | Gansow et al. |
| 4,474,893 | 10/1984 | Reading |
| 4,490,473 | 12/1984 | Brunhouse |
| 4,578,360 | 3/1986 | Smith |
| 4,661,444 | 4/1987 | Li |
| 4,664,911 | 5/1987 | Uhr et al. .................. 424/85.91 |
| 4,676,980 | 6/1987 | Segal et al. .................. 424/85.91 |
| 4,714,681 | 12/1987 | Reading |
| 4,722,892 | 2/1988 | Meares et al. |
| 4,741,900 | 5/1988 | Alvarez et al. .................. 436/548 |
| 4,760,142 | 7/1988 | Primes et al. .................. 544/287 |
| 4,863,713 | 9/1989 | Goodwin et al. .................. 424/1.1 |

FOREIGN PATENT DOCUMENTS

| | | |
|---|---|---|
| 0136835 | 10/1985 | European Pat. Off. |
| 0177191 | 4/1986 | European Pat. Off. |
| 0217577 | 4/1987 | European Pat. Off. |
| 2515046 | 10/1982 | France |
| 8102522 | 9/1981 | PCT Int'l Appl. |
| 8303679 | 10/1983 | |
| 8504811 | 11/1985 | PCT Int'l Appl. |
| WO86/01407 | 3/1986 | PCT Int'l Appl. |

OTHER PUBLICATIONS

Embleton et al., Antibody Targeting of Anti-Cancer Agents, Chap. 16, Monoclonal Antibodies for Cancer Detection & Therapy, 1985, Academic Press, pp. 317-344.

Goldin, et al., Quantitation of Antibody Binding to Cell Surface Antigens by X-Ray Fluorescence Spectrometry, Biochimica et Biophysica Acta, 552 (1979) pp. 120-128.

Parker, Charles W., Radioimmunoassay of Biologically Active Compounds. 1976, Prentice Hall, Inc. pp. 101-104.

(List continued on next page.)

Primary Examiner—David Saunders
Attorney, Agent, or Firm—Browdy and Neimark

[57] ABSTRACT

Immunological reagents, consisting of a) antibody or fragment conjugates having both an anti-cell specificity and an anti-hapten specificity, and b) synthetic tracers containing at least two hapten sites and at least one site suitable to attach radioactive isotopes, paramagnetic ions, drugs or toxins, are provided. These reagents are capable of binding to target cells in a specific way, and the tracer localizes preferentially on the membrane of antigen-bearing cells, even in the presence of excess antibody conjugate (affinity enhancement). These reagents are usefully employed, either in vitro or in vivo, to detect tumors, metastases, or other tissue injuries, when the synthetic tracer carries radioactive or paramagnetic compounds, and to kill target cells when the synthetic tracer carries radioactive compounds or drugs or toxins.

25 Claims, 1 Drawing Sheet

OTHER PUBLICATIONS

Mauer et al., Proteins & Polypeptides as Antigens, Methods of Enzymology, vol. 70, Edited by Vunakis & Langone, Academic Press, 1980, p. 50.

Green, et al., Detection of Antibody Monomers, Dimers, & Polymers Upon Divalent Haptens Biochem. and Biophys. Res. Comm. vol. 46, No. 2, 1972, pp.738–744.

Hnatowich, et al, "Radioactive Labeling of Antibody: A Simple and Efficient Method", Science, vol. 220, pp. 613–615, 1983.

Goodwin, "Antibody-Hapten Complexes for Imaging", *Radio Labeled Monoclonal Antibodies for Imaging and Therapy*, Nato Advanced Study Institute, p. 9.

Ohgushi, et al. "Dextran-Magnetite: A New Relaxation Reagent and Its Application to $T_2$ Measurements in Gel Systems", *Journal of Magetic Resonance*, pp. 599–601 (1978).

Pecq, et al, "DNA Polyintercalating Drugs": DNA Binding of Diacridine Deriviatives, *Proc. Nat. Acad. Sci. USA*, vol. 72, No. 8, pp. 2915–2919, 1975.

Curtet, et al. "Selective Modification of NMR Relaxation Time in Human Colorectal Carcinoma by Using Gadolinium Diethylenetriaminepentaacetic Adic Conjugated with Monoclonal Antibody 19-9", *Proc. Natl. Acad. Sci.*, vol. 83, pp. 4277–4281, Jun. 1986.

Kohler, et al. "Continuous Cultures of Fused Cells Secreting Antibody of Predefined specificity", *Nature*, vol. 256, Aug. 7, 1975, pp. 495–497.

Unger, et al, "Magetic Resonance Imaging Using Gadolinium Labeled Monoclonal Antibody", *Investigative Radiology*, vol. 20, pp. 693–700, 1985.

Lamoyi, et al, "Preparation of F(ab')$_2$ Fragments from Mouse IgG of Various Subclasses", *Journal of Immunological Methods*, vol. 56, pp. 235–243, 1983.

Rearden et al, "Antibodies Against Metal Chelates", *Letters to Nature*, vol. 316, pp. 265–268, 1985.

Hunter et al, "Preparation of Iodine-131 Labelled Human Growth Hormone of High Specific Activity", *Nature*, vol. 194, No. 4827, pp. 495–496, 1962.

Bradwell et al, "Limiting Factors in the Localization of Tumours with Radiolabelled Antibodies", *Immunology Today*, vol. 6, No. 5, pp. 163–170, 1985.

Gatter, "The Differential Diagnosis of Routinely Processed Anaplastic Tumors Using Monoclonal Antibodies", *American Journal of Clinical Pathology*, vol. 82, No. 1, pp. 33–43, 1984.

AFFINITY ENHANCEMENT IMMUNOLOGICAL REAGENTS FOR IN VIVO DETECTION AND KILLING OF SPECIFIC TARGET CELLS

FIELD OF THE INVENTION

The present invention relates generally to specific immunological reagents including monoclonal antibodies that recognize human target cells. In one aspect, this invention relates to the use of radioactive or paramagnetic compounds in association with antibodies for immunodiagnostic purposes. In another aspect, it relates to the use of radioactive materials, or drugs, or toxins, or enzymes in association with antibodies for immunotherapy of cellular disorders, particularly cancer.

BACKGROUND OF THE INVENTION

The use of antibodies labeled with radioactive iodine isotopes has been proposed to detect tumor-associated antigens. For instance, in the U.S. Pat. No. 3,927,193 labeled goat anti-human carcino-embryonic antigen antibodies have been injected to Syrian hamsters inoculated with human carcinoma and shown to localize preferentially in the tumor. It was thus suggested that labeled antibodies might be used to visualize tumors after injection to patients using detectors available in the art. Such diagnostic applications are commonly refered to as immunodiagnostic. As early as 1956, Beierwaltes and coworkers cured a patient with advanced malignant melanoma by injecting large amounts of $^{131}$I-labeled gamma-globulins from a rabbit immunized with the patients' own tumor cells. Further use of directly labeled polyclonal antibodies has not met with equal success. For convenience, this, and other related applications of antibodies, will be refered to as immunotherapy.

Since the discovery of monoclonal antibodies (Köhler and Milstein), monoclonal antibodies capable of specific binding to cells of a particular type, or, in a less specific way, to cells of a few different types, have been obtained in many laboratories and industries. Such monoclonal antibodies are most attractive because they are homogeneous and potentially more specific than polyclonal antibodies extracted from antisera. They have been widely used to identify cells in tissue sections and various biological samples, and to diagnose cancer and metastases in vitro (Gatter et al.). An obvious application of these reagents was to label them with a suitable radioactive isotope and inject them in animals or human in order to visualize in vivo specific cell subsets (e.g. tumors or metastases) using existing devices such as the gamma camera. Another application was to inject large quantities of monoclonal antibodies labeled with radioactive isotopes capable of killing the cells (e.g. malignant cells) to which the antibody became bound.

Isotopes generally used in radioimmunoscintigraphy are: $^{131}$iodine and $^{123}$iodine (covalently coupled to tyrosines of the antibody, Hunter and Greenwood); $^{111}$indium, $^{99m}$Tc and other metals (attached directly or by means of suitable chelating agents covalently coupled to the antibody, Hnatowich et al.). For radioimmunotherapy, high linear energy transfer (LET) isotopes are usually preferred (e.g. $^{131}$I, $^{211}$At, $^{212}$Bi).

The state of the art and the major limitations of radioimmunoscintigraphy and radioimmunotherapy have been discussed by Bradwell et al. The essential parameters in these techniques are the fraction of the injected dose specifically localized at the site(s) where target cells are present and the uptake ratio (i.e. the ratio of the concentration of specifically bound antibody to that of the radioactivity present in surrounding normal tissues). These parameters are related in a non-trivial way. Usually the fraction of injected dose localized in the tumor is not much better than 0.1%, and contrast not better than 2 to 3. These figures translate in the common observation that tumors (or other tissue injuries) smaller than 1 to 2 cm in diameter cannot be detected, and that radioimmunotherapy has met with little success so far. Non specific uptake by non-target organs such as the liver, kidneys or bone-marrow is another major limitation of the technique, especially for radioimmunotherapy, where irradiation of the bone marrow often causes the dose-limiting toxicity.

Recently, the use of low molecular weight tracers, such as indium chelates, associated with dual specificity antibody conjugates combining antibodies (or fragments) to the target cells with antibodies (or fragments) to the indium chelate, has been proposed (Reardan et al.). Increased uptake ratios and faster localization of the tracer are expected, since the radioactivity would be associated to low molecular weight structures capable of fast distribution through the body tissues and of rapid clearance. If the radioactive isotope has a rapid radioactive decay, such as $^{123}$I or $^{99m}$Tc, images recorded sooner after injection will be obtained with higher activities remaining than with the conventional techniques. Similarly, fast localization and rapid clearance of excess radioactive isotopes, or drugs or toxins would reduce damage to normal cells and tissues in immunotherapy.

However, the tracer may be effectively trapped by excess circulating dual specificity conjugate, and its specific localization and its clearance would be impaired. This is a major limitation of the proposed two-step technique in immunodiagnostic and immunotherapy. To take advantage of the theoretical potential of the method, excess dual specificity conjugate should be removed from the circulation prior to injection of the tracer (Goodwin). This would involve cumbersome in vivo manipulations, which have not been substantiated yet. Thus further improvements of the method are still required.

Other useful techniques for the diagnosis of cancer and tissue injuries which do not necessarily involve the use of antibodies are known to the art. In addition to the techniques derived from X-ray radiography, of which an elaborated version is the computer assisted tomography (CAT scanning), sophisticated detectors have been developed to monitor the magnetic resonance properties of living organisms, and particularly to produce images of organs or whole bodies in a technique called Magnetic Resonance Imaging (MRI). The association of the exquisite spatial resolution of MRI and the specificity of immunological reagents such as the monoclonal antibodies has been contemplated (Unger et al., Curtet et al.). It has been proposed to label monoclonal antibodies to specific cellular antigens with chemical groups capable of enhancing the relaxation of the protons contained in body tissues and fluids, and particularly to use paramagnetic metal ions such as Fe, Mn, or Gd. However, the technique is far from achieving clinically useful results, particularly because the concentrations of relaxation agents that must be deposited at the target sites are very high. Theoretically, the problem would be solved by conjugating several thousand relaxation agents per antibody molecule, but this has not been possible yet without compromising the ability of the antibody to recognize the antigen. Thus, in this area also, substantial advances must occur.

In an entirely different domain of the prior art, a few natural multivalent ligands are recognized to bind more tightly to multivalent receptors than the corresponding monovalent ligands (e.g. binding of IgE and IgM to cell membrane receptors, binding of agregated IgG to the polymeric Fc receptor, or C1q binding to immune complexes). Similarly, synthetic multivalent ligands for receptors such as the DNA have been described (Le Pecq et al.) with increased affinity as compared to the monovalent ligand. However, no useful application of this knowledge has been proposed in the fields of in vivo immunodiagnostic or immunotherapy.

BIBLIOGRAPHY

Patent Documents

Hansen H. J., Prinus F. J., Localization of tumors by radiolabelled antibodies (1975), U.S. Pat. No. 3,927,193.

Adams T. H., David G. S., Halpern S. E., Anticorps monoclonaux marqués par un radionucléide et leur application àla visualisation d'une tumeur (1982), French Patent No. 2,515,046.

Gansow O. A., Strand M., Metal chelate conjugated monoclonal antibodies (1982), U.S. Pat. No. 4,472,509.

Gansow O. A., Strand M., Use of metal chelate conjugated antibodies (1982), U.S. Pat. No. 4,454,106.

Meares C. F., David, G. S., Monoclonal antibodies against metal chelates (1984), International Patent No. WO 86/01407.

Reading C. L., Recombinant Monoclonal Antibodies (1984), U.S. Pat. No. 4,474,893.

Martinis J., Bartholomew R. M., Davud G. S., Adams T. H., Fincke J. M., Antibodies having dual specificities, their preparation and use therefor (1983), International Patent no. WO 83/03679.

Other Publications

Köhler G., Milstein C., Continuous cultures of fused cells secreting antibodies of pre-defined specificity (1975), Nature, 256, 496–497.

Gatter K. C., Alcock C., Heryet A., Pulford K. A., Heyderman E., Taylor-Papadimitriou J., Stein H., Mason D. Y., The differential diagnosis of routinely processed anaplastic tumors using monoclonal antibodies (1984), Amer. J. Clin. Pathol., 82, 33–43.

Bradwell A. R., Fairweather D. S., Dykes P. W., Keeling A., Vaughn A., Taylor J., Limiting factors in localization of tumours with radiolabeled antibodies (1985), Immunol. Today, 6, 163–170.

Reardan D. T., Meares C. F., Goodwin D. A., McTigue M., David G. S., Stone M. R., Leung L. P., Bartholomew R. M., Frerich J. M., Antibodies against metal chelates (1985), Nature, 316, 265–268.

Hunter W. N., Greenwood F. C., Preparation of iodine[131] labelled growth hormone of high specific activity (1962), Nature, 194, 495–496.

Hnatowich D. J., Layne W. W., Chids R. L., Lanteigne D., Davis M. A., Radioactive labelling of antibody: a simple and efficient method (1983), Science, 220, 613–615.

Goodwin D. A., Antibody-hapten complexes for imaging. (1986), Nato Advanced Study Institute "Radio-labeled monoclonal antibodies for imaging and therapy", p. 9.

Lamoyi E., Nisonoff A., Preparation of F(ab')$_2$ fragments from IgG of various subclasses (1983), J. Immunol. Methods, 56, 235–243.

Unger, E. C., et al. Magnetic resonance imaging using gadolinium labeled monoclonal antibody (1985), Invest. Radiol., 20, 693–700.

Curtet, C., et al. Selective modification of NMR relaxation time in human colorectal carcinoma by using gadolinium-diethylenetriaminepentaacetic acid conjugated with monoclonal antibody 19-9. (1986) Proc. Natl. Acad. Sci. USA, 83, 4277–4281.

Le Pecq J. B., Le Bret M., Barbet J., Roques B. P. DNA polyintercalating drugs: DNA binding of diacridine derivatives (1975), Proc. Natl. Acad. Sci. USA, 72, 2915–2919.

Ohgushi M., Nagayama K., Wada A., Dextranmagnetite: a new relaxation reagent and its application to $T_2$ measurements in gel systems (1978), J. Magnet. Res., 29, 599–601.

SUMMARY OF THE INVENTION

Figure 1:
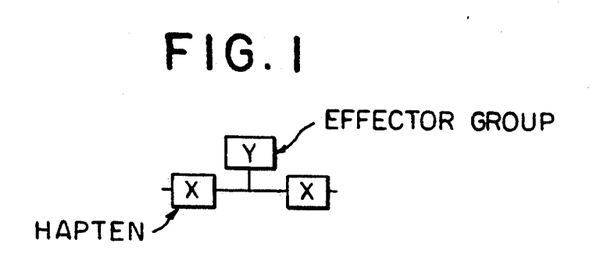
FIG. 1 illustrates a general structure of affinity enhancement probes.
Figure 2:
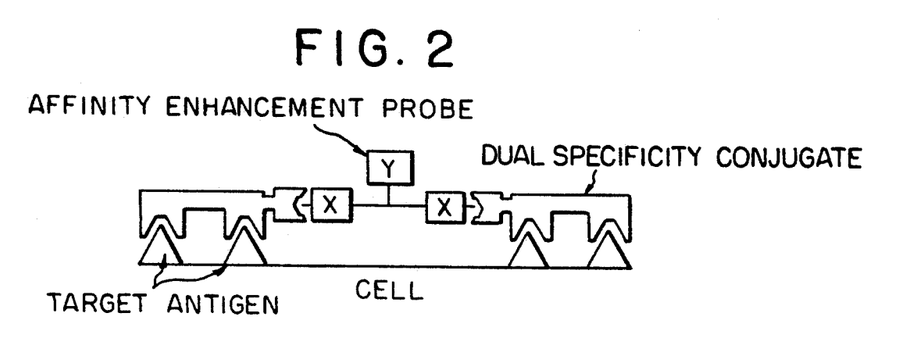
FIG. 2 shows a multivalent complex comprising two or more molecules of dual specificity conjugates bound to specific antigen.
Figure 3:
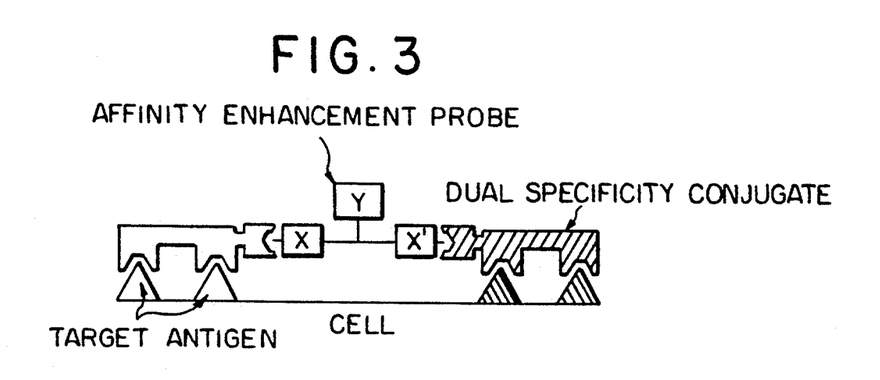
FIG. 3 illustrates an affinity enhancement probe made with two different haptens.

The present invention is based upon an entirely new approach using low molecular weight tracers with definite tropism towards cell-bound, as opposed to excess free, dual specificity conjugate. Thus tracers possessing such a tropism have been designed by taking advantage of the fact that multiple simultaneous binding to receptors distributed at the external side of the membrane of target cells may be much stronger than monovalent binding to the same receptors in solution.

a) It is an object of the present invention that reagents, referred to as dual specificity conjugates, may be provided to associate to target cells (defined by their expression of a given membrane antigen) receptors for soluble ligands (haptens).

b) It is another object of the present invention that binding of the dual specificity conjugates to antigens expressed at the surface of the target cells result in a distribution of receptors for the soluble ligands within the surface of the cell membrane that may behave as a potential multivalent receptor for the soluble ligands.

c) It is a further object of the present invention to provide low molecular weight molecules, referred to as affinity enhancement probes, suitable for radioisotopic labeling, or carrying paramagnetic compounds, or drugs or toxins.

d) It is still a further object of the present invention that the affinity enhancement probe comprises at least two hapten groups and one or several effector groups. The said effector groups are either suitable for radiolabeling, or comprise one or several paramagnetic compounds, or drugs, or toxins. A general structure of the affinity enhancement probes may be schematized as follows, where X refers to any suitable hapten, Y to any suitable effector group, the lines refering to any sequence of atoms or chemical groups linked by covalent chemical bonds and forming a single stable molecule:

For some particular application, the hapten and the effector group may be one and a single entity. In that case, the affinity enhancement probe may be constituted of two, or more, of this hapten/effector group linked together through covalent chemical bonds.

e) It is still a further object of the present invention that the affinity enhancement probes, as described in b) are capable of binding specifically to the target cells, properly treated with dual specificity conjugate as described in a).

f) It is an other object of the present invention that multivalent complexes comprising two or more molecules of dual specificity conjugates and at least one molecule of the affinity enhancement probe may become bound to the specific antigens expressed at the surface of the target cells. Such multivalent complexes may be usefully schematized as follows, wherein X, Y and the solid lines have the meanings described in d), and the dual specificity conjugate is represented as an F(ab')$_2$, recognizing a cell membrane target antigen, coupled to an Fab' recognizing the hapten X: as shown in FIG. 2.

g) It is still another object of the present invention that the affinity enhancement probe is made with two different, non cross-reactive, haptens (X and X'). In that case, two different dual specificity conjugates, one with specificity to one cellular antigen and to hapten X, a second with specificity to another cellular antigen and hapten X' are used. As a result the affinity enhancement probe will react preferentially with cells expressing both cellular antigens, as opposed to those expressing only one or the other. This is shown more clearly in FIG. 2.

h) It is still another object of the present invention that specific binding of the affinity enhancement probe is not precluded by the presence of excess dual specificity conjugate present in the surrounding medium.

i) It is still another object of the present invention that these reagents may be used to detect or kill specific cells in animals and human for immunodiagnosis, magnetic resonance imaging, and immunotherapy.

These and other objects of the present invention are provided by dual specificity conjugate associating receptors for cell membrane antigens and soluble ligands, particularly by antibodies or fragments recognizing cell membrane antigen(s) covalently coupled to antibodies or fragments recognizing a soluble hapten (dual specificity conjugate), and by synthetic molecules, suitable for radioisotopic labeling or carrying paramagnetic compounds, or drugs, or toxins, presenting two, or more, hapten groups (affinity enhancement probe). Preferred embodiments of the present invention are monoclonal antibodies and their fragments as the receptors for cell-surface antigens or as hapten-specific receptors. Other preferred embodiments of the present invention are F(ab')$_2$ fragments as the cell-specific antibody and Fab' fragments as the hapten specific receptor. Other preferred embodiments of the present invention are dinitrophenyl (DNP) groups as the hapten, and tyrosines or chelating agents as the group suitable for radioactive labeling.

DETAILED DESCRIPTION OF THE PREFERRED EMBODIMENTS

Monoclonal antibodies with specificity to tumor-specific or tumor-associated antigens, or to cell-surface antigens of specific organs, or to serum proteins, or to muscular proteins, or to any other normal or pathologic constituents of the human body are useful in preparing the dual specificity conjugate. Monoclonal antibodies against tumor-associated antigens of melanoma, or T-cell lymphoma, or breast, or lung, or colorectal cancer, or clotting antigens such as fibrin, or intracellular antigens such as villin or myosin, or viral or microbial antigens are preferred. The specificity and binding affinity of each such monoclonal antibody with respect to its target antigen may be about that of monoclonal antibodies conventionally used for the binding assay being performed. High affinity monoclonal antibodies (dissociation constant smaller than $10^{-8}$M) are preferred.

Monoclonal antibodies to a wide variety of small molecular weight haptens of natural or synthetic origin are known or may be produced by techniques known to the previous art. Preferred monoclonal antibodies recognize specifically dinitrophenyl group of succinyl-histamine, or metal chelates. Most preferred anti-hapten monoclonal antibodies exhibit an affinity toward the monomeric hapten that does not allow the circulating dual specificity conjugate to trap the affinity enhancement probe before it binds to target associated dual specificity conjugate. Typically, the most preferred dissociation constant of each such antibody is choosen between $10^{-9}$ and $10^{-7}$M.

The monoclonal antibodies may be produced from tissue culture supernatants or from animal implanted tumors, and purified in large quantities according to well-established techniques. It is advantageous for the present invention to hydrolyze them by limited enzymatic digestion, under defined conditions, to yield fragments of various molecular sizes, of which some retain the ability to bind the antigen. Most preferred fragments are F(ab')$_2$ fragments of about 100,000 Da, or Fab or Fab' fragments of about 50,000 Da which can be prepared and purified using techniques known to previous art.

Monoclonal antibodies, or their fragments, may be reacted with a variety of heterobifunctional reagents capable of cross-linking the cell-reactive antibody to the hapten reactive antibody. For example, succinimidyl 4-(N-maleimidomethyl)cyclohexane-1-carboxylate (SMCC) or succinimidyl 3-(2-pyridyldithio)propionate (SPDP) are suitable to attach to one antibody or fragment a thiol-reactive group. The other antibody or fragment may be derivatized in such a way as to attach a thiol group. A preferred embodiment is to generate a thiol group by partial reduction of the antibody, or, most preferably, of its F(ab')$_2$ fragment. Mixtures of the two in appropriate molar ratios and incubation conditions result in the formation of conjugate which has the requisite properties for the present invention. Particularly, it exhibits good stability in various media, including aqueous buffers, tissue culture media and body fluids under reasonable conditions of pH and temperature. In addition, it is able to bind the hapten and the cells for which it has specificity. Alternatively, dual specificity antibodies may be produced by somatic fusion of hybridoma cells producing antibodies of two different specificities, as claimed in the U.S. Pat. No. 4,474,893 and in the International patent WO 83/03679.

Any hapten to which monoclonal antibodies are available or may be produced may be suitable for the present invention. Those haptens which are not present in human tissues are preferred. Also preferred are haptens which are not degraded too rapidly after in vivo administration and those which do not present too high a toxicity to animals or humans. Two or more haptens and at least one effector group may be linked together in a single molecule by any chemical or enzymatic procedure. Those procedures that result in a uniquely defined chemical structure are preferred. Structures in which the distance between two hapten groups may be larger than 25 Å are also preferred. An example of suitable chemical structure is provided by peptides of small molecular weight whose side chains and terminal amino and/or carboxylate residues are substituted by the haptens and the effector groups. Peptides which contain one or several D-amino acids are preferred. The preferred chemical structure is one which allows radiolabeling with a radioisotope suitable for radioimmunoimaging or radioimmunotherapy. Most preferred structures are those in which a phenol or phenyl group is present. In that case, labeling may be performed with radioactive isotopes of the halogens such as, for example, $^{18}F$, $^{76}Br$, $^{77}Br$, $^{123}I$, $^{125}I$, $^{131}I$, $^{211}At$. In that case too, preferred radioactive isotopes are $^{123}I$ for diagnosis and $^{131}I$ or $^{211}At$ for therapy. Other most preferred structures are those in which one or several chelating group have been introduced. In that case, a radioactive metal cation may be used as a label, such as, for example, $^{67}Co$, $^{67}Ga$, $^{68}Ga$, $^{67}Cu$, $^{90}Y$, $^{97}Ru$, $^{99m}Tc$, $^{111}In$, $^{113m}In$, $^{203}Pb$, $^{212}Bi$. In that case too, preferred radioactive isotopes are $^{111}In$ or $^{99m}Tc$ for diagnosis and $^{90}Y$ or $^{212}Bi$ for therapy.

In another aspect of the invention, a stable paramagnetic ion, such as Gd, Fe, Mn, may be used. Another suitable structure is one which carries one or several paramagnetic compounds such as, for instance, paramagnetic ions (e.g. Gd, Fe, or other heavy metals), or stable free radicals (e.g. derivatives of the nitroxide radical).

Superparamagnetic complexes such as those produced by precipitation of magnetite in the presence of dextran are also suitable (Ohgushi et al.).

Alternatively the radiolabeled or paramagnetic moiety of the tracer may serve as a hapten, as, for instance, when a chelating agent is used to bind $^{111}In$, $^{99m}Tc$, or a stable paramagnetic metal such as Gd, or any other metal isotope. In that case two or more chelated metals should be included into the tracer molecule.

In all cases, the radioactive or stable isotope may be introduced after the synthesis of the non-labeled tracer has been completed, as in the case of tyrosine radioiodination or radioisotopic metal chelation, or before.

Still another suitable structure is one which associates in the same molecule two or more haptens and one or several molecules of a cytotoxic drug or toxin. Preferred cytotoxic drug are methotrexate, a derivative of the antitumor Vinca alkaloids, or of the platinum complexes, or of the anthracycline. A suitable toxin may be a plant or bacterial toxin or its separated toxic A chain, such as diphtheria toxin, ricin, abrin, gelonin, or pokeweed antiviral protein.

A preferred hapten is the dinitrophenyl group. A suitable affinity enhancement probe is represented by the following chemical structure:

Another suitable affinity enhancement probe is represented by the following chemical structure:

A preferred procedure for the use of the reagents of the present invention is intravenous injection of a suitable dose of dual specificity conjugate, together with, or followed after a time delay of a few minutes to several hours by, injection of the radioactive affinity enhancement probe at a dose adjusted to allow detection of the target cells by the imaging device, or killing of the target cells. The imaging device may be either a detector of radioactivity available in the art, or a magnetic resonance imaging apparatus also available in the art. In immunotherapy applications of the present invention, the cytotoxic effector group, which may be a radioactive nucleide, a drug or a toxin, will localize onto the target cells and exert its action with or without being internalized by the said target cells.

The preferred time delay between injection of the dual specificity conjugate and of the affinity enhancement probe may be adjusted to allow localization of the dual specificity conjugate at the target site and partial clearance of the excess. One of the major advantages of the present invention over techniques according to previous art, is that clearance of the excess dual specificity conjugate is not required prior injection of the tracer. Accordingly, this time delay may be very short. For radioimmunodiagnostic applications, imaging may be performed a few hours after injection of the affinity enhancement probe, at a time when optimum localization has been achieved. This time may be selected according to the pharmacokinetic properties of the affinity enhancement probe, the radioactive decay of the isotopes and the rate at which the affinity enhancement probe is able to localize at the specific target sites. As mentioned above, the affinity enhancement system is particularly useful when the radioactive isotope has fast radioactive decay.

Preparation of several embodiments of the present invention will be more particularly described hereafter.

EXAMPLE 1

SYNTHESIS OF THREE DUAL SPECIFICITY CONJUGATES (COMPOUNDS 1 to 3)

Purification of monoclonal antibodies.

The anti-CALLA antibody, a mouse monoclonal IgG$_1$, clone ALB1, the anti-CD5 antibody, a mouse monoclonal IgG$_{2a}$, clone BL1a, the anti-Lyb8.2 antibody, a mouse monoclonal IgG$_1$, clone CY34, and the anti-2,4 dinitrophenyl (DNP) antibody, a mouse monoclonal IgG$_{2a}$, clone U7-27, are purified from ascites fluid by affinity chromatography on protein A-Sepharose (Pharmacia).

Preparation of F(ab')$_2$ fragments.

The anti-CALLA antibody (clone ALB1, 2 to 5 mg/ml) is dialyzed once against 10 mM formate buffer pH 2.8, then once against 50 mM acetate buffer pH 4.2. Pepsin (crystallized x2, Calbiochem), 5% w/w, is then added and allowed to react for 2 h at 37° C. (Lamoyi and Nisonoff). The mixture is fractionated by ion-exchange chromatography on a Mono S column (Pharmacia), equilibrated with 50 mM acetate buffer pH 4.5. Elution is obtained with a linear gradient of NaCl (0 to 0.6M). The F(ab')$_2$ fragment of the anti-Lyb8.2 antibody (clone CY34) is prepared according to the same technique. The anti-CD5 (clone BL1a) and anti-DNP (clone U7.27) antibodies are dialyzed against 10 mM acetate buffer pH 3.8 and 5% (w/w) pepsin is added. Digestion is performed over 5 h at 37° C. and stopped by raising the pH to 8 with 2M Tris-HCL buffer pH 8.5. The F(ab')$_2$ fragments are separated from intact IgG and Fc fragments by affinity chromatography on protein A-Sepharose.

Fab' fragment of the anti-DNP antibody.

The F(ab')$_2$ fragment of the anti-DNP antibody is dialyzed against 0.1M phosphate buffer pH 6.0 and cysteamine is added to a final concentration of 10 mM. After 1 h at 37° C., the resulting Fab' fragment is purified by gel filtration on a TSK 3000 SW HPLC column (LKB) equilibrated with 0.1M phosphate buffer pH 6.0 supplemented with 5 mM EDTA.

Derivatization with SMCC.

To the F(ab')$_2$ fragments (2 to 5 mg/ml) is added a 10 fold molar excess of SMCC (10 mg/ml in dimethylformamide) and the mixture is incubated for 1.5 h at 30° C. After centrifugation (2 min, 10,000 g), the mixture is made free of excess SMCC by gel filtration on a PD10 column (Pharmacia) equilibrated with 0.1M phosphate buffer pH 6.0.

Preparation of the anti-CD5-anti-DNP dual specificity conjugate (compound 1).

The anti-DNP Fab' and the SMCC-derivatized anti-CD5 F(ab')$_2$ are mixed in a 2 to 1 molar ratio. The mixture is concentrated by ultrafiltration under positive pressure and allowed to react at 4° C. for 24 h. The dual specificity conjugate is separated from unreacted F(ab')$_2$ and Fab' by gel filtration on a TSK 3000 SW column in 0.1M phosphate buffer pH 6.0. The fraction corresponding to an apparent molecular weight around 150,000 Da is collected and stored at −20° C. (compound 1). Conjugates between the F(ab')$_2$ fragments of the anti-CALLA or the anti-Lyb8.2 antibodies and the Fab' fragment of the anti-DNP antibody have been prepared according to the same technique (compound 2 and 3 respectively).

EXAMPLE 2

SYNTHESIS OF CHELATING DIMERIC AND MONOMERIC PROBES (COMPOUNDS 4 AND 5)

Synthesis of bis-(N-ε-(2,4-dinitrophenyl)-L-Lysyl)-diethylenetriamine-pentaacetic acid (compound 4)

To a solution of DNP-Lysine (1.2 mmol in 10 ml of a 1:1 mixture of 100 mM borate pH 8.5 and dimethylformamide) are added 0.6 mmol of DTPA cyclic anhydride. The mixture is allowed to react overnight at room temperature, and evaporated to dryness under reduced pressure. The residue is redissolved in 10 ml of water and excess HCl (1M) is added. The precipitate is redissolved in water by addition of NaOH (1M) and further purified by ion exchange chromatography on an FPLC mono Q (Pharmacia) column. Compound 4 has an rF of 0.15 by thin layer chromatography (TLC) on silica gel in n-butanol:acetic acid:water (4:1:1). Some (N-ε-(2,4-dinitrophenyl)-L-Lysyl)-diethylenetriamine-pentaacetic acid (compound 5) is formed as a by-product (rF=0.05). Both products have been further purified by HPLC on a C18 reverse phase column using a 1:1 mixture of 0.05% trifluoroacetic acid in water and methanol. Compound 4 and 5 have been shown to be able to chelate $^{111}$In by TLC on silica gel in methanol:10% ammonium acetate (1:1).

EXAMPLE 3

SYNTHESIS OF RADIOIODINATED DIMERIC AND MONOMERIC PROBES (COMPOUNDS 6 AND 7)

Synthesis of N-hydroxysuccinimide 2,4-dinitrophenyl-aminocaproate.

2,4-dinitrophenyl-aminocaproic acid (300 mg) is dissolved in 6 ml of dioxane and N-hydroxysuccinimide, 120 mg in 4 ml of ethyl acetate, is added. N,N'-dicylohexylcarbodiimide, 200 mg in 2 ml of dioxane, is added, and the mixture is allowed to react for 3 h at room temperature. The precipitate which forms during the reaction is filtered off and the solution is evaporated to dryness under reduced pressure. The yellow residue is crystallized in boiling absolute ethanol. The yellow needles of the N-hydroxysuccinimide ester are collected and dried (Rf=0.59 by TLC in chloroform:ethyl acetate, 1:1 on silica gel).

Synthesis of N-α-(2,4-dinitrophenyl-aminocaproyl)-L-tyrosyl-N-ε-(2,4-dinitrophenyl-aminocaproyl)-L-lysine (compound 6).

L-tyrosyl-L-lysine (10 mg) is dissolved in 1 ml of 50 mM Hepes buffer pH 8.0, a three fold molar excess of N-hydroxysuccinimide 2,4-dinitrophenyl-aminocaproate in 2 ml of dioxane is added, and the mixture is allowed to react for 16 h at room temperature. After lyophilization, the mixture is redissolved in 1 ml of water and acidified with 1N HCl. The precipitate is crystallized in boiling absolute ethanol (Rf=0.80 in n-butanol/acetic acid/water 4/1/1). Further purification of compound 6 is obtained by HPLC on a C18 ultrosphere ODS column with 60% methanol, 40% trifluoroacetic acid (0.05% in water).

Iodination of compound 6:

Compound 6 (2 nmol) is dissolved in 100 $\mu$l of 50 mM phosphate 150 mM NaCl buffer pH 7.3 supplemented with 20% ethanol and transferred into a small plastic tube containing 10 $\mu$g of Iodogen. Na$^{131}$I (1 mCi) is added and the reaction is continued for 30 min at room temperature. The monoiodo-derivative of compound 6 is purified by HPLC on C18 column with 70% methanol, 30% trifluoroacetic acid (0.05% in water).

Synthesis of N-$\alpha$-(2,4-dinitrophenyl-aminocaproyl)-L-tyrosyl-gylicine (compound 7).

L-tyrosyl-glycine (10 mg) is dissolved in 1 ml of 50 mM Hepes buffer pH 8.0, a 1.5 fold molar excess of N-hydroxysuccinimide 2,4-dinitrophenyl-aminocaproate in 2 ml of dioxane is added, and the mixture is allowed to react for 16 h at room temperature. After lyophilization, the mixture is redissolved in 1 ml of water and acidified with 1N HCl. The precipitate (compound 7, Rf=0.72 in n-butanol/acetic acid/water 4/1/1) is purified by HPLC on a C18 ultrosphere ODS column with 60% methanol, 40% trifluoroacetic acid (0.05% in water).

Iodination of compound 7:

Compound 7 is radiolabeled under the same conditions as compound 6. Purification of the monoiodo derivative is performed by HPLC using the same column but with 50% methanol, 50% trifluoroacetic acid (0.05% in water).

EXAMPLE 4

A)-SPECIFIC BINDING OF THE AFFINITY ENHANCEMENT PROBE TO TARGET CELLS IN VITRO IN THE PRESENCE OF EXCESS DUAL SPECIFICITY CONJUGATE

Experimental conditions.

In an Eppendorf plastic tube are incubated 100 $\mu$l of a cell suspension at 3.10$^7$ cells/ml of a human T-cell line (HPBALL) or of a human B lymphoma line (Namalwa) in phosphate buffered saline supplemented with 0.1% bovine serum albumin, 0.02% azide and 50 mM deoxyglucose, 100 $\mu$l of a solution of dual specificity conjugate, anti-CD5 (compound 1) or anti-CALLA (compound 2), at 0.5 $\mu$g/ml in the same buffer and 150 $\mu$l of radioiodinated compound 6 or compound 7. After 3 h at 4° C. or 37° C. with agitation, 100 $\mu$l of the resulting cell suspension are transferred into triplicate 0.4 ml plastic tubes containing 200 $\mu$l of a 1.2:1 mixture of dibutyl-phthalate and ethyl-hexyl-phthalate. After 30 sec centrifugation at 10,000 g, 50 $\mu$l of the supernatant are collected and counted, and the bottom of the tube, containing the cell pellet, is cut and counted. Results are then expressed as bound/free percentages.

Results.

The experimental settings allow cross-controlled experiments, since HPBALL cells express the T-cell marker CD5, but not the tumor-associated antigen CALLA, whereas Namalwa cells express CALLA, but not CD5.

| Cell | Temperature | Bound/free (%) | | | | | |
|---|---|---|---|---|---|---|---|
| | | Dimer | | | Monomer | | |
| | | 1 + 6 | 2 + 6 | SB | 1 + 7 | 2 + 7 | SB |
| HPBALL (1+, 2−) | 4° C. | 72 | 16 | 56 | 38 | 3 | 35 |
| | 37° C. | 67 | 15 | 52 | 12 | 3 | 9 |
| Namalwa (1+, 2−) | 4° C. | 2 | 23 | 21 | 2 | 6 | 4 |
| | 37° C. | 4 | 21 | 17 | 1 | 5 | 4 |

(SB = Specific Binding)

B)-SPECIFIC BINDING OF THE AFFINITY ENHANCEMENT PROBE TO TARGET CELLS IN VITRO AFTER WASHING THE EXCESS DUAL SPECIFICITY CONJUGATE

Experimental conditions.

The experimental conditions are similar to that described above but the dual specificity conjugate is incubated first for 1 h, then the cells are washed 3 times and the tracer is added. The cells are then pelleted after another 2 h incubation. Results.

| Cell | Temperature | Bound/free (%) | | | | | |
|---|---|---|---|---|---|---|---|
| | | Dimer | | | Monomer | | |
| | | 1 + 6 | 2 + 6 | SB | 1 + 7 | 2 + 7 | SB |
| HPBALL (1+, 2−) | 37° C. | 45 | 9 | 36 | 11 | 3 | 7 |
| Namalwa (1+, 2−) | 4° C. | 15 | 145 | 130 | 8 | 50 | 42 |
| | 37° C. | 4 | 11 | 7 | 2 | 4 | 2 |

(SB = Specific Binding)

EXAMPLE 5

Compound 4, and the monomeric analogue, compound 5, (0.2 nmol) have been labeled with 0.2 mCi of $^{111}$In chloride by incubation at room temperature in 0.1M citrate buffer for 30 min. The mixture is then diluted into phosphate buffered saline and used without further manipulation. After incubation of freshly isolated BALB/c mouse spleen cells (10$^7$ cells/ml) at 37° C. for 2 h in the presence of anti-Lyb8.2-anti-DNP conjugate (compound 3) at 3.10$^{-9}$M, binding of the labeled compounds 4 and 5 was monitored as described in example 4. Under these conditions, 26% (bound/free) of labeled compound 4 became bound to the mouse spleen cells (of which about 70% are Lyb8.2 positive), as opposed to only 6% (bound/free) of the monomeric tracer (compound 5). In the absence of conjugate, the non-specific binding of the labeled tracers was about 0.2%.

Examples 4 and 5 demonstrate that:

1) the tracers (affinity enhancement probes), as defined in the present invention (compound 4 and 6), become bound to the target cells at either 4° C. and 37° C., provided that the cell have been preincubated with the specific dual specificity conjugate (in the experiments presented above: anti-CD5 for HPBALL cells, anti-CALLA for Namalwa cells, anti-Lyb8.2 for BALB/c mouse spleen cells).

2) the presence of excess specific dual specificity conjugate does not prevent specific binding of the affinity enhancement proges (compounds 4 and 6).

3) tracers (compound 5 and 7) prepared with the same hapten DNP and radiolabeled to the same specific activity, but presenting a single hapten group exhibit much less specific binding to the target cells in these assays, especially at 37° C.

4) comparable results are obtained using radioiodinated tracers (compounds 6 and 7) and tracers derived from a chelating agent with a bound radioactive metal, $^{111}$In, (compounds 4 and 5).

The effect described above cannot be taken as a particular behavior of the experimental system selected as an example. On the contrary, the target cells express low amounts of target antigen at their membrane ($2.10^4$ CALLA antigens for Namalwa cells, $4.10^5$ CD5 antigens for HYBALL cells, and $3.10^4$ Lyb8.2 antigens for BALB/c mouse spleen cells). Most tumor or normal cells that would be selected as targets for in vivo diagnostic or therapeutic applications will express at least similar amounts of target antigen. The excellent results obtained with the affinity enhancement probes demonstrate that the affinity enhancement system will be extremely advantageous in such applications.

While certain specific embodiments have been disclosed in the foregoing description, it will be understood that various modifications within the scope of the invention may occur to those skilled in the art. Therefore, it is intended that adoptions and modifications should and are intended to be comprehended within the scope of the appended claims.

We claim:

1. A method for delivering to predetermined antigens of desired target cells, in vivo, a detectable substance or a toxic substance capable of killing target cells, comprising:
    (a) administering a dual specificity antibody conjugate comprising a first monoclonal antibody or fragment conjugated to a second monoclonal antibody or fragment, said first monoclonal antibody or fragment having binding affinity for said predetermined antigen on the desired target cells, and said second monoclonal antibody or fragment having binding affinity for a predetermined hapten;
    (b) without administration of a clearing agent intended to remove circulating antibody conjugates, administering an affinity enhancement probe comprising at least two of said predetermined haptens, said haptens being covalently linked together in a uniquely defined chemical structure, said affinity enhancement probe further having at least one said detectable substance or toxic substance bound thereto.

2. A method in accordance with claim 1, wherein said affinity enhancement probe comprises only two predetermined haptens.

3. A method in accordance with claim 1, wherein said affinity enhancement probe comprises only one said detectable or toxic substance.

4. A method in accordance with claim 1, wherein said second monoclonal antibody or fragment is an Fab or Fab' fragment.

5. A method in accordance with claim 1, wherein said first monoclonal antibody or fragment is an F(ab')$_2$, Fab' or Fab fragment.

6. A method in accordance with claim 1, wherein said affinity enhancement probe contains a chelating agent which can be labeled with metal cations.

7. A method in accordance with claim 1, wherein said predetermined antigen is a tumor-associated antigen.

8. A method in accordance with claim 1, wherein said predetermined antigen is a cell-associated antigen.

9. A method in accordance with claim 1 for delivering a radioactive isotope to predetermined antigens on the desired target cells, wherein said detectable substance or toxic substance bound to said affinity enhancement probe is a radioactive isotope.

10. A method in accordance with claim 9, wherein said affinity enhancement probe contains a phenol group and said radioactive isotope is a radioactive halogen covalently attached to the phenol group of said affinity enhancement probe.

11. A method for killing desired cells bearing predetermined antigens, in vivo, comprising:
    delivering, in accordance with claim 1, a toxic substance to the predetermined antigens on the desired target cells, wherein the detectable substance or toxic substance bound to said affinity enhancement probe is a toxic substance.

12. A method in accordance with claim 11, wherein said toxic substance is a radioactive isotope, a drug or a toxin.

13. A method in accordance with claim 1, wherein said haptens are linked together by means of a peptide.

14. A method in accordance with claim 13, wherein said peptide contains at least one D-amino acid.

15. A method in accordance with claim 1, wherein said step of administering a dual specificity conjugate comprises administering a mixture of two different conjugates, wherein the first monoclonal antibodies or fragments of said two different conjugates have binding affinity for different predetermined antigens on said desired target cells and the second monoclonal antibodies or fragments of said two different conjugates have binding affinity for different haptens, and wherein said haptens of said affinity enhancement probe include each of the haptens toward which the second monoclonal antibodies or fragments of said two different conjugates are specific.

16. A method in accordance with claim 15, wherein at least one of the haptens of said affinity enhancement probe includes a 2,4-dinitrophenyl group.

17. A method in accordance with claim 15, wherein one said predetermined antigen is a tumor associated antigen and the other said predetermined antigen is a different tumor associated antigen or a cell- or tissue-associated antigen.

18. A method for imaging of desired target cells bearing predetermined antigens, comprising:
    delivering, in accordance with claim 1, a detectable substance to the predetermined antigens of the desired target cells, wherein the detectable substance or toxic substance bound to said affinity enhancing probe is a detectable substance, and
    detecting the detectable substance, thereby imaging the desired target cells.

19. A method in accordance with claim 18, wherein said detectable substance is a radioactive isotope.

20. A method in accordance with claim 18, wherein said detectable substance comprises paramagnetic metal ions and said detecting step comprises detecting nuclear magnetic resonance relaxation by a magnetic resonance imaging device.

21. A method in accordance with claim 1, wherein each of said predetermined haptens on said affinity enhancement probe is the same.

22. A method in accordance with claim 21, wherein each of the haptens of said affinity enhancement probe includes a 2,4-dinitrophenyl group.

23. A method in accordance with claim 21, wherein said affinity enhancement probe has the structure:

24. A method in accordance with claim 21, wherein said affinity enhancement probe has the structure:

25. A method for delivering to predetermined antigens of desired target cells, in vivo, a detectable substance or a toxic substance capable of killing target cells, comprising:
(a) administering a mixture of two different dual specificity antibodies each comprising a first monoclonal antibody or fragment conjugated to a second monoclonal antibody or fragment, said first monoclonal antibodies or fragments of said two different conjugates having binding affinity for different ones of said predetermined antigens on the desired target cells, and said second monoclonal antibodies or fragments of said two different conjugates having binding affinity for different predetermined haptens;
(b) without administration of a clearing agent intended to remove circulating antibody conjugates, administering an affinity enhancement probe comprising at least two different haptens which are covalently linked to one another, wherein said haptens of said affinity enhancement probe include each of the haptens toward which said second monoclonal antibodies or fragments of said two different conjugates are specific, said affinity enhancement probe further having at least one said detectable substance or toxic substance bound thereto.

* * * * *